(12) United States Patent
Murugan et al.

(10) Patent No.: US 9,850,208 B2
(45) Date of Patent: Dec. 26, 2017

(54) PROCESS FOR MAKING 2-CHLORO-5-METHYLPYRIDINE

(71) Applicant: Vertellus Specialties Inc., Indianapolis, IN (US)

(72) Inventors: Ramiah Murugan, Indianapolis, IN (US); Martin Grendze, Indianapolis, IN (US)

(73) Assignee: Vertellus Holdings LLC, Indianapolis, IN (US)

( * ) Notice: Subject to any disclaimer, the term of this patent is extended or adjusted under 35 U.S.C. 154(b) by 0 days.

(21) Appl. No.: 15/114,304

(22) PCT Filed: Jan. 27, 2015

(86) PCT No.: PCT/US2015/013075
§ 371 (c)(1),
(2) Date: Jul. 26, 2016

(87) PCT Pub. No.: WO2015/113043
PCT Pub. Date: Jul. 30, 2015

(65) Prior Publication Data
US 2017/0008846 A1  Jan. 12, 2017

Related U.S. Application Data

(60) Provisional application No. 61/931,746, filed on Jan. 27, 2014.

(51) Int. Cl.
*C07D 213/61* (2006.01)
*C07D 213/803* (2006.01)

(52) U.S. Cl.
CPC ....... *C07D 213/61* (2013.01); *C07D 213/803* (2013.01)

(58) Field of Classification Search
CPC .................................................. C07D 213/61
See application file for complete search history.

(56) References Cited

U.S. PATENT DOCUMENTS

| 4,661,555 A | 4/1987 | Koga et al. |
| 4,897,488 A * | 1/1990 | Gallenkamp ........ C07D 213/61 546/345 |
| 5,010,201 A | 4/1991 | Kaufmann et al. |
| 7,342,115 B2 | 3/2008 | Hutchison et al. |

FOREIGN PATENT DOCUMENTS

| EP | 0941989 | 7/2009 |
| WO | 95/15313 | 6/1995 |

OTHER PUBLICATIONS

Sorgi, K. L. "2,2,6,6-Tetramethylpiperidine." in e-EROS Encyclopedia of Reagents for Organic Synthesis Published Online: Apr. 15, 2001.*
Xue Jiangsu Huagong, 2008, 36(5), 33-34 (with English abstract).*
Xue "Production Process Improvement of 2-Chloro-5-Methylpyridine" "2—Lu—5—Jiaji—Biding Shengchan Gongyi Gaijin" Jiangsu Huagong, 2008, 36(5), 33-34 [English translation] is attached.*
PCT Search Report and Written Opinion for PCT/US2015/013075, dated Apr. 15, 2015.

* cited by examiner

*Primary Examiner* — David K O'Dell
(74) *Attorney, Agent, or Firm* — Barnes & Thornburg LLP

(57) ABSTRACT

Processes for the preparation of 2-chloro-5-methylpyridine are described.

14 Claims, No Drawings

PROCESS FOR MAKING 2-CHLORO-5-METHYLPYRIDINE

CROSS-REFERENCE TO RELATED APPLICATIONS

This application is a national stage entry made under 35 U.S.C. §371(b) of PCT International Application No. PCT/US2015/013075, filed Jan. 27, 2015, which claims the benefit under 35 U.S.C. §119(e) of U.S. Provisional Application No. 61/931,746, filed Jan. 27, 2014, the disclosures of which are incorporated by reference herein in their entirety.

TECHNICAL FIELD

The invention described herein pertains to improved processes for preparing 2-chloro-5-methylpyridine.

2-Chloro-5-methylpyridine is a useful intermediate in the production of pharmaceutical compounds and agricultural pesticides. Several processes for preparing this useful compound have been described. For example, see WO1995015313 and the references cited therein.

It is known that 2-chloro-5-methylpyridine is obtained in addition to the other isomers, 2-chloro-3-methylpyridine, 4-chloro-3-methylpyridine and 3-chloro-5-methylpyridine by reacting 3-methylpyridine N-oxide with phosphorus oxychloride (cf. Weissberger, Chemistry of Heterocyclic Compounds, Pyridine and its Derivatives, Vol. 14, Supplement, Part 2, p. 112). The main product of this reaction is 4-chloro-3-methylpyridine and the percentage of 2-chloro-5-methylpyridine is in general below 25%. U.S. Pat. No. 4,897,488 describes the preparation of 2-chloro-5-methylpyridine from 3-methylpyridine 1-oxide using phosphorus oxychloride ($POCl_3$) in the presence of a basic organic nitrogen compound and a diluent at a temperature between about −50° C. and 50° C. Additionally, U.S. Pat. No. 5,099,025 describes the preparation of 2-chloro-5-methylpyridine, which involves reacting the 3-methylpyridine N-oxide with sulfonyl or sulfamoyl chlorides in the presence of a basic organic nitrogen compound and a diluent at a temperature between about −120° C. and 150° C. Although these processes offer an improvement over the reaction of 3-methylpyridine N-oxide with phosphorus oxychloride described by Weissberger, the yields and the ratios of 2-chloro-5-methylpyridine to 2-chloro-3-methylpyridine obtained by these methods are such that here remains a continued need for improved processes for preparing 2-chloro-5-methylpyridine with increased yield and/or increased purity.

Described herein are improved processes for the preparation of 2-chloro-5-methylpyridine (I) from 3-methylpyridine N-oxide (II) with improved yield and decreased levels of impurities, including the isomeric 2-chloro-3-methylpyridine.

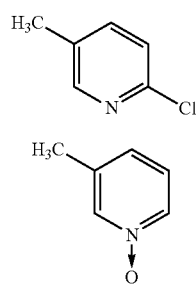

Several illustrative embodiments of the invention are described by the following clauses:

A process for preparing 2-chloro-5-methylpyridine, the process comprising the step of:
(a) contacting 3-methylpyridine N-oxide in a diluent, at a first temperature of about −20° C. to about 20° C., with $POCl_3$, and a hindered cyclic amine base of formula (III)

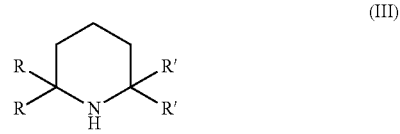

wherein R and R' are independently selected in each instance from hydrogen and C1-C4 alkyl, and where at least one R is not hydrogen and at least one R' is not hydrogen.

The process of the preceding clause further comprising the step of:
b) contacting the 3-methylpyridine N-oxide in the diluent with aluminum chloride ($AlCl_3$) prior to contacting with $POCl_3$, and the hindered cyclic amine.

A process for preparing 2-chloro-5-methylpyridine, the process comprising the step of:
(a) contacting 3-methylpyridine N-oxide in a diluent, at a temperature of about −20° C. to about 20° C., with $POCl_3$, aluminum chloride ($AlCl_3$), and a hindered cyclic amine base of formula (III)

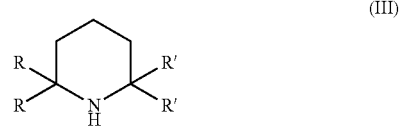

wherein R and R' are independently selected in each instance from hydrogen and C1-C4 alkyl, and where at least one R is not hydrogen and at least one R' is not hydrogen.

The process of either of the two preceding clauses wherein the amount of $AlCl_3$ per mole of 3-methylpyridine N-oxide is about 0.1 mole to about 0.3 mole.

The process of the preceding clause wherein the amount of $AlCl_3$ per mole of 3-methylpyridine N-oxide is about 0.2 mole to about 0.25 mole.

The process of any one of the preceding clauses wherein the diluent is selected from pentane, hexane, heptane, octane, cyclohexane, methylcyclohexane, petroleum ether, naphtha, ligroin, benzene, toluene, xylenes, methylene chloride, chloroform, tetrachloromethane, 1,2-dichloroethane, chlorobenzene, dichlorobenzene, diethyl ether, dipropyl ether, diisopropyl ether, dibutyl ether, methyl tert-butyl ether, glycol dimethyl ether, diglycol dimethyl ether, tetrahydrofuran, dioxane, methyl acetate, ethyl acetate, propyl acetate, butyl acetate amyl acetate, acetonitrile, and propionitrile.

The process of any one of the preceding clauses wherein the diluent is methylene chloride.

The process of any one of the preceding clauses wherein the amount of $POCl_3$ per mole of 3-methylpyridine N-oxide is about 1 to about 5 moles.

The process of any one of the preceding clauses wherein the amount of $POCl_3$ per mole of 3-methylpyridine N-oxide is about 1.5 to about 2.5 moles.

The process of any one of the preceding clauses wherein the amount of POCl$_3$ per mole of 3-methylpyridine N-oxide is about 2 moles.

The process of any one of the preceding clauses wherein the amount of the hindered cyclic amine per mole of 3-methylpyridine N-oxide is about 1 to about 5 moles.

The process of any one of the preceding clauses wherein the amount of the hindered cyclic amine per mole of 3-methylpyridine N-oxide is about 1.5 to about 2.5 moles.

The process of any one of the preceding clauses wherein the amount of the hindered cyclic amine per mole of 3-methylpyridine N-oxide is about 2 moles.

The process of any one of the preceding clauses wherein at least one R and at least one R' is methyl.

The process of any one of the preceding clauses wherein each R and R' is methyl.

The process of any one of the preceding clauses further comprising the step of
b) heating the resulting mixture from step a) to a second temperature while removing a portion of the diluent by distillation.

The process of any one of the preceding clauses further comprising the step of
c) holding the mixture resulting from step b) at the second temperature for a period of time, wherein the second temperature is from about 50° C. to about 150° C.

In any of the embodiments described herein, approximately 2 moles each of phosphorus oxychloride and hindered cyclic amine per mole of 3-methylpyridine N-oxide is used.

As used herein diluent generally refers to a organic solvent that is inert to POCl$_3$, AlCl$_3$, and the hindered cyclic amine base under the conditions of the process described herein. Solvents useful for the processes described herein illustratively include, but are not limited to, halogenated or non-halogenated hydrocarbons, such as pentane, hexane, heptane, octane, cyclohexane, methylcyclohexane, petroleum ether, naphtha, ligroin, benzene, toluene, xylenes, methylene chloride, chloroform, tetrachloromethane, 1,2-dichloroethane, chlorobenzene and dichlorobenzene, ethers such as diethyl ether, dipropyl ether, diisopropyl ether, dibutyl ether, methyl tert.butyl ether, glycol dimethyl ether, diglycol dimethyl ether, tetrahydrofuran and dioxane, esters such as methyl acetate, ethyl acetate, propyl acetate, butyl acetate and amyl acetate, and nitriles such as acetonitrile and propionitrile.

In any of the embodiments of the processes described herein, the 3-methylpyridine N-oxide can be initially introduced in a diluent and, with stirring and cooling, the POCl$_3$, dissolved in the diluent, and the hindered cyclic amine, also dissolved in the diluent, are added to the reaction mixture at a convenient rate, at the same time ("simultaneously", "in parallel"). In any of the embodiments described herein the addition of the POCl$_3$ is begun before the addition of the hindered cyclic amine so that between 5% and 20% of the POCl$_3$ is already present in the reaction mixture by the time the addition of the hindered cyclic amine is started.

In an alternative embodiment of the processes described herein 3-methylpyridine N-oxide in a diluent can be added at a convenient rate to a mixture of POCl$_3$ and the hindered cyclic amine in the diluent. As used herein, "added at a convenient rate" generally means adding at a rate which allows the reaction to proceed while maintaining a desired temperature range for the reaction mixture during the addition. External heating or cooling may be used in maintaining a desired temperature range.

Work-up and isolation of the product can be carried out using any conventional manner known to one of skill in the art. In any of the embodiments of the processes described herein water can be added to the reaction mixture with stirring and cooling, the diluent can be removed, e.g. by distillation, the aqueous phase can be adjusted to a pH of about 5-6 with an aqueous alkali metal or alkaline earth metal hydroxide solution such as, for example, sodium hydroxide solution, and the reaction product can be largely removed from this mixture by steam distillation. In some embodiments, the organic portion of the steam distillate contains the product 2-chloro-5-methylpyridine.

The following examples further illustrate specific embodiments of the invention; however, the following illustrative examples should not be interpreted in any way to limit the invention.

EXAMPLES

The following abbreviations are used below, in addition to those abbreviations which are commonly used in the art, chloromethylpyridine, CMP, 2-chloro-5-methylpyridine, 2C5MP, 2-chloro-3-methylpyridine, 2C3MP, 4-chloro-3-methylpyridine, 4C3MP, 2,2,6,6-tetramethylpiperidine, TMP, 3-methyl-pyridine-N-oxide, 3-PNO In the following examples, after workup of the reaction mixture, the crude, wet chloromethylpyridines were recovered from the reaction mixture by steam distillation (crude yield).

Example 1

A 2-L flask was charged with 3-methyl-pyridine-N-oxide (3-PNO) (38.2 g, 0.35 mol), CH$_2$Cl$_2$ (742.0 g, 560 ml), and cooled to 0-5° C., 10% of a solution of phosphorus oxychloride (POCl$_3$) (107.4 g, 0.7 mol) in CH$_2$Cl$_2$ (93.3 g, 70 ml) was added to the flask. The remaining POCl$_3$ solution and a solution of diisooctylamine (DIOA) (169.0 g, 0.7 mol) in CH$_2$Cl$_2$ (92.8 g, 70 ml) were added to the flask over a 3 hour period at 0-5° C. The mixture was stirred for 2 hours at 0-5° C. Water (105.2 g) was slowly added to the flask holding the temperature at or below 20° C. The mixture was stirred for 30 minutes then CH$_2$Cl$_2$ was removed by distillation (600 ml) to a pot temperature of 67° C. The mixture was cooled to 25° C. 20% NaOH solution (392.2 g) was added to the reaction mixture to a pH of 5.6. Water (101.4 g) was then added to the flask and the product was recovered by steam distillation.

Conversion of 3-PNO=99.9%; crude product=75.1 g; yield of 2C5MP=14%; ratio 2C5MP/2C3MP=1.1/1

Example 2

A 2-L flask was charged with 3-PNO (38.2 g, 0.35 mol) and CH$_2$Cl$_2$ (742.4 g, 560 ml). The mixture was cooled to 0-5° C. A solution of POCl$_3$ (108.1 g, 0.705 mol) in CH$_2$Cl$_2$ (92.8 g, 70 ml) was made and 10% of this solution was added to the flask at 0-5° C. The remaining POCl$_3$ solution and a solution of 2,2,6,6-tetramethylpiperidine (TMP, 98.9 g, 0.7 mol) were added co-currently to the flask over a 3 hour period at 0-5° C. The mixture was stirred at 0-5° C. for 2 hours, and allowed to stand overnight at room temperature. Water (105.0 g) was carefully added to the flask holding the temperature at or below 25° C. The mixture was stirred 30 minutes. CH$_2$Cl$_2$ was removed by distillation from the flask to a pot temperature of 60° C. 20% NaOH (405.5 g) was added to the reaction mixture to a pH of 5.2 holding the temperature at 30-35° C. The product was recovered by steam distillation.

Conversion of 3-PNO=100%; crude product=41.1 g; yield of 2C5MP=74.3%; ratio 2C5MP/2C3MP=17.7/1

Example 3

A 2-L flask was charged with 3-PNO (38.2 g, 0.35 mol) and $CH_2Cl_2$ (744.1 g, 560 ml). The mixture was cooled to 0-5° C. 10% of a solution of $POCl_3$ (107.3 g, 0.7 mol) in $CH_2Cl_2$ (93.1 g, 70 ml) was added to the flask at 0-5° C. The remaining $POCl_3$ solution and a solution of dicyclohexylamine (126.9 g, 0.7 mol) in $CH_2Cl_2$ (92.8 g, 70 ml) were added co-currently to the flask over a 3 hour period at 0-5° C. The mixture was stirred for 2 hours at 0-5° C., and allowed to stand overnight at room temperature. Water (105.0 g) was carefully added to the flask holding temperature below 30° C. The mixture was stirred 30 minutes. $CH_2Cl_2$ was removed by distillation to a pot temperature of 50° C. The mixture was cooled to 25-30° C. 20% NaOH (380.4 g) was added to a pH of 5.2 holding the temperature below 40° C. The product was recovered by steam distillation.

Conversion of 3-PNO=100%; crude product=46.8 g; yield of 2C5MP=63.2%; ratio 2C5MP/2C3MP=5.0/1

Example 4

A 2-L flask was charged with 3-PNO (38.2 g, 0.35 mol) and $CH_2Cl_2$ (742.0 g, 560 ml). The mixture was cooled to 0-5° C. 10% of a solution of $POCl_3$ (107.3 g, 0.7 mol) in $CH_2Cl_2$ (92.8 g, 70 ml) was added to the flask at 0-5° C. The remaining $POCl_3$ solution and a solution of 2,6-lupetidine (79.4 g, 0.7 mol) in $CH_2Cl_2$ (93.0 g, 70 ml) were added to the flask co-currently at 0-5° C. over a 3 hour period. The mixture was stirred at 0-5° C. for 2 hours, allowed to slowly warm to room temperature and to stand at room temperature over the weekend. Water (105.0 g) was carefully added to the flask holding the temperature at or below 35° C. The mixture was stirred for 30 minutes. $CH_2Cl_2$ was removed by distillation until the pot temperature was 60° C. The mixture was cooled to 25° C. 20% NaOH (401.3 g) was added to the reaction mixture to a pH of 5.2 holding the temperature at or below 35° C. The product was recovered by steam distillation.

Conversion of 3-PNO=100%; crude product=49.0 g; yield of 2C5MP=64.9%; ratio 2C5MP/2C3MP=2.9/1

Example 5

A 2-L flask was charged with 3-PNO (38.2 g, 0.35 mol) and $CH_2Cl_2$ (742.3 g, 560 ml). The mixture was cooled to 0-5° C. 10% of a solution of $POCl_3$ (107.3 g, 0.7 mol) in $CH_2Cl_2$ (92.8 g, 70 ml) was added to the flask at 0-5° C. The remaining $POCl_3$ solution and a solution of N,N-diisopropylethylamine (90.5 g, 0.7 mol) in $CH_2Cl_2$ (92.9 g, 70 ml) were added to the flask co-currently at 0-5° C. over a 3 hour period. The mixture was stirred for 2 hours at 0-5° C., allowed to slowly rise to room temperature and stirred overnight. Water (105.1 g) was carefully added to the flask holding the temperature at or below 35° C. The mixture was stirred 30 minutes. $CH_2Cl_2$ was removed by distillation until the pot temperature was 60° C. The mixture was cooled to 30° C. 20% NaOH (430.7 g) was added to the reaction mixture to a pH of 5.0 holding the temperature at or below 35° C. The product was recovered by steam distillation.

Conversion of 3-PNO=100%; crude product=62.6 g; yield of 2C5MP=45.7%; ratio 2C5MP/2C3MP=9.3/1

Example 6

A 2-L flask was charged with 3-PNO (38.3 g, 0.351 mol), tetramethylammonium chloride (9.6 g, 0.088 mol), and $CH_2Cl_2$ (744.9 g, 560 ml). The mixture was cooled to 0-5° C. 10% of a solution of $POCl_3$ (107.7 g, 0.702 mol) in $CH_2Cl_2$ (92.8 g, 70 ml) was added to the flask at 0-5° C. The remaining $POCl_3$ solution and a solution of diisopropylamine (70.8 g, 0.7 mol) $CH_2Cl_2$ (92.8 g, 70 ml) were added co-currently to the flask over a 3 hour period at 0-5° C. The mixture was stirred at 0-5° C. for 2 hours, allowed to slowly warm to room temperature and stirred overnight. Water (105.1 g) was carefully added to the flask holding the temperature at or below 30° C. The mixture was stirred for one hour. $CH_2Cl_2$ was removed by distillation to a pot temperature of 65° C. The mixture was cooled to <40° C. 20% NaOH (403.2 g) was added to the reaction mixture to a pH of 5.2 holding temperature below 40° C. The product was recovered by steam distillation.

Conversion of 3-PNO=100%; crude product=46.1 g; yield of 2C5MP=64.9%; ratio 2C5MP/2C3MP=5.4/1

Example 7

A 2-L flask was charged with 3-PNO (38.2 g, 0.35 mol) and $CH_2Cl_2$ (742.0 g, 560 ml). The mixture was cooled to 0-5° C. 10% of a solution of $POCl_3$ (107.3 g, 0.7 mol) in $CH_2Cl_2$ (92.8 g, 70 ml) was added to the flask at 0-5° C. The remaining $POCl_3$ solution and a solution of diisopropylamine (35.7 g, 0.353 mol) and N,N,N,N-tetramethyl-1,8-naphthalenediamine (proton sponge; 75.0 g, 0.35 mol) in $CH_2Cl_2$ (93.2 g, 70 ml) were added to the flask at 0-5° C. over a 3 hour period. The mixture was stirred at 0-5° C. for 2 hours, allowed to slowly warm to room temperature and stirred overnight. Water (105.1 g) was carefully added to the flask holding temperature below 35° C. The mixture was stirred 30 minutes. $CH_2Cl_2$ was removed by distillation to a pot temperature of 60° C. The mixture was cooled to 40° C. 20% NaOH (400.5 g) was added to the reaction mixture at or below 40° C. raising the pH to 5.7. The product was recovered by steam distillation.

Conversion of 3-PNO=100%; crude product=54.4 g; yield of 2C5MP=63.4%; ratio 2C5MP/2C3MP=5.3/1

Example 8

A 2-L flask was charged with 3-PNO (38.2 g, 0.35 mol) and $CH_2Cl_2$ (742.0 g, 560 ml). The mixture was cooled to 0-5° C. 10% of a solution of $POCl_3$ (107.3 g, 0.7 mol) in $CH_2Cl_2$ (93.1 g, 70 ml) was added to the flask at 0-5° C. The remaining $POCl_3$ solution and a solution of 2,2,6,6-tetramethylpiperidine (98.9 g, 0.7 mol) in $CH_2Cl_2$ (92.8 g, 70 ml) were added simultaneously to the flask at 0-5° C. over a 3 hour period. The mixture was stirred at 0-5° C. for 2 hours, allowed to slowly warm to room temperature and stirred overnight. Water (105.0 g) was carefully added to the flask holding the temperature below 40° C. The mixture was cooled and stirred for 30 minutes. $CH_2Cl_2$ was removed by distillation to a pot temperature of 60° C. The mixture was cooled to 35° C. 20% NaOH (408.8 g) was added to the reaction mixture at or below 35° C. to a pH of 4.9. The product was recovered by steam distillation.

Conversion of 3-PNO=100%; crude product=45.9 g; yield of 2C5MP=79.8%; ratio 2C5MP/2C3MP=19.6/1

Example 9

A 2-L flask was charged with 3-PNO (24.3 g, 0.223 mol) and $CH_2Cl_2$ (472.4 g, 356 ml). The mixture was cooled to 0-5° C. 10% of a solution of $POCl_3$ (68.6 g, 0.447 mol) in $CH_2Cl_2$ (59.2 g, 45 ml) was added to the flask at 0-5° C. The remaining $POCl_3$ solution and a solution of N-tert-butylisopropylamine (51.3 g, 0.445 mol) in $CH_2Cl_2$ (59.6 g, 45 ml) were added simultaneously to the flask at 0-5° C. over a period of 3 hour. The mixture was stirred at 0-5° C. for 2 hours then allowed to slowly warm to room temperature and stir overnight. Water (66.8 g) was carefully added to the flask while holding the temperature at or below a maximum of 35° C. The resulting mixture was stirred for 30 minutes. The mixture was heated and $CH_2Cl_2$ removed by distillation to a pot temperature of 68° C. The mixture was cooled to 24° C. 20% NaOH (263.1 g) was added to the reaction mixture at or below 35° C. to a pH of 5.0. The product was recovered by steam distillation.

Conversion of 3-PNO=100%; crude product=30.7 g; yield of 2C5MP=63.5%; ratio 2C5MP/2C3MP=9.1/1

Example 10

A 2-L flask was charged with 3-PNO (38.4 g, 0.352 mol) and $CH_2Cl_2$ (742.4 g, 560 ml). The mixture was cooled to 0-5° C. 10% of a solution of $POCl_3$ (107.5 g, 0.701 mol) in $CH_2Cl_2$ (92.8 g, 70 ml) was added to the flask at 0-5° C. The remaining $POCl_3$ solution and a solution of hexamethyldisilazane (113.0 g, 0.7 mol) in $CH_2Cl_2$ (92.8 g, 70 ml) were added simultaneously to the flask at 0-5° C. over a 3 hour period. The mixture was stirred at 0-5° C. for 2 hours then allowed to slowly warm to room temperature and stirred overnight. Water (155.0 g) was carefully added to the flask. The mixture was stirred for 30 minutes then $CH_2Cl_2$ was removed by distillation to a pot temperature of 60° C. The mixture was cooled to 20° C. 20% NaOH (432.2 g) was added to the reaction mixture to pH of 5.2. Recovered product by steam distillation.

Conversion of 3-PNO=100%; crude product=67.2 g; yield of 2C5MP=0.9%; ratio 2C5MP/2C3MP=1.2/1

Example 11

A 2-L flask was charged with 3-PNO (38.2 g, 0.35 mol) and $CH_2Cl_2$ (742.3 g, 560 ml). Aluminum chloride ($AlCl_3$) (11.7 g, 0.088 mol) was added in portions to the flask. Exothermic reaction, solution addition was performed slowly. The mixture was cooled flask to 0-5° C. 10% of a solution of $POCl_3$ (107.3 g, 0.7 mol) in $CH_2Cl_2$ (93.3 g, 70 ml) was added to the flask at 0-5° C. The remaining $POCl_3$ solution and a solution of diisopropylamine (71.0 g, 0.702 mol) in $CH_2Cl_2$ (92.8 g, 70 ml) were added co-currently to the flask at 0-5° C. The mixture was stirred at 0-5° C. for 2 hours, allowed to slowly warm to room temperature and stirred overnight. Water (105.0 g) was carefully added to the flask holding temperature at or below 35° C. The mixture was stirred 30 minutes. $CH_2Cl_2$ was removed by distillation to a pot temperature of 60° C. The mixture was cooled to 25° C. 20% NaOH (416.2 g) was added to the reaction mixture to a pH of 5.0 while holding the temperature at or below 35° C.

Conversion of 3-PNO=100%; crude product=50.2 g; yield of 2C5MP=84.4%; ratio 2C5MP/2C3MP=8.3/1

Example 12

A 2-L flask was charged with 3-PNO (38.2 g, 0.35 mol) and $CH_2Cl_2$ (742.0 g, 560 ml). $AlCl_3$ (11.7 g, 0.088 mol) was added in portions to the flask. Exothermic reaction. The mixture was cooled flask to 0-5° C. 10% of a solution of $POCl_3$ (107.4 g, 0.7 mol) in $CH_2Cl_2$ (92.9 g, 70 ml) was added to the flask at 0-5° C. The remaining $POCl_3$ solution and a solution of 2,2,6,6-tetramethylpiperidine (98.9 g, 0.7 mol) in $CH_2Cl_2$ (92.9 g, 70 ml) were added to the flask simultaneously at 0-5° C. over a 3 hour period. The mixture was stirred for 2 hours at 0-5° C., allowed to slowly warm to room temperature and stirred overnight. Water (105.2 g) was carefully added to the flask holding the temperature below 35° C. The mixture was stirred for 30 minutes. $CH_2Cl_2$ was removed by distillation to a pot temperature of 60° C. The mixture was cooled to 35° C. 20% NaOH (479.8 g) was added to the flask holding the temperature at or below 40° C. to a pH of 5.2. The product was recovered by steam distillation.

Conversion of 3-PNO=100%; crude product=53.3 g; yield of 2C5MP=93.5%; ratio 2C5MP/2C3MP=21.7/1

Example 13

A 2-L flask was charged with 3-PNO (38.2 g, 0.35 mol) and $CH_2Cl_2$ (742.1 g, 560 ml). The mixture was cooled to about 8° C. $AlCl_3$ (15.4 g, 0.116 mol) was added in portions to the flask. The temperature of the mixture reached 24° C. during the addition. The mixture was cooled to 0-5° C. 10% of a solution of $POCl_3$ (107.8 g, 0.703 mol) in $CH_2Cl_2$ (92.8 g, 70 ml) was added to the flask at 0-5° C. The remaining $POCl_3$ solution and a solution of diisopropylamine (70.9 g, 0.701 mol) in $CH_2Cl_2$ (92.8 g, 70 ml) were added simultaneously to the flask at 0-5° C. over a 3 hour period. The mixture was stirred at 0-5° C. for 2 hours then allowed to slowly warm to room temperature. The mixture was stirred over the weekend. Water (105.2 g) was carefully added to the flask holding the temperature at or below 30° C. The mixture was stirred for 30 minutes. $CH_2Cl_2$ was removed by distillation to a pot temperature of 66° C. The mixture was cooled to 40° C. 20% NaOH (417.4 g) was added to the flask holding the temperature at or below 40° C. to a pH of about 5. The product was recovered by steam distillation.

Conversion of 3-PNO=99.9%; crude product=45.8 g; yield of 2C5MP=76.6%; ratio 2C5MP/2C3MP=7.3/1

Example 14

A 2-L flask was charged with 3-PNO (38.2 g, 0.35 mol) and $CH_2Cl_2$ (742.0 g, 560 ml). The mixture was cooled to about 0° C. $AlCl_3$ (46.7 g, 0.35 mol) was added to the flask in portions holding the temperature below 20° C. The mixture was cooled to 0-5° C. 10% of a solution of $POCl_3$ (107.3 g, 0.7 mol) in $CH_2Cl_2$ (93.0 g, 70 ml) was added to the flask at 0-5° C. The remaining $POCl_3$ solution and a solution of diisopropylamine (70.8 g, 0.7 mol) in $CH_2Cl_2$ (92.8 g, 70 ml) were added to the flask simultaneously at 0-5° C. over a 3 hour period. The mixture was stirred at 0-5° C. for 2 hours then allowed to slowly warm to room temperature and stirred overnight. Water (105.1 g) was carefully added to the flask holding temperature at <35° C. The mixture was stirred for 30 minutes. $CH_2Cl_2$ was removed by distillation until the pot temperature reached 62°

C. The mixture was cooled below 40° C. 20% NaOH (499.5 g) and additional H$_2$O (150 ml) were added to the reaction mixture to a pH of 5.5.

Conversion of 3-PNO=99.8%; crude product=42.3 g; yield of 2C5MP=61.8%; ratio 2C5MP/2C3MP=3.4/1

Example 15

A 2-L flask was charged with 3-PNO (76.4 g, 0.7 mol) and CH$_2$Cl$_2$ (699.0 g). The mixture was cooled to 0-5° C. AlCl$_3$ (21.0 g, 0.157 mol) was added to the flask and rinsed in w/CH$_2$Cl$_2$ (43.2 g). Exothermic reaction-temperature reached 25° C. The mixture was cooled to 0-5° C. Solution of POCl$_3$ (155.6 g, 1.015 mol) in CH$_2$Cl$_2$ (92.8 g, 70 ml) and diisopropylamine (105.5 g, 1.043 mol) in CH$_2$Cl$_2$ (92.9 g, 70 ml) were added to the flask simultaneously over a 3 hour period at 0-5° C. The mixture was stirred for 2 hours at 0-5° C. and then allowed to slowly warm to room temperature and stirred overnight. Water (181.7 g) was carefully added to the flask holding the temperature below 35° C. The mixture was stirred for 30 minutes then CH$_2$Cl$_2$ was removed by distillation to a pot temperature of 60° C. The mixture was cooled below 40° C. 20% NaOH (630.4 g) was added to the reaction mixture to a pH of 5.1. The product was recovered by steam distillation.

Conversion of 3-PNO=100%; crude product=86.0 g; yield of 2C5MP=72.2%; ratio 2C5MP/2C3MP=6.0/1

Example 16

A 2-L flask was charged with 3-PNO (76.4 g, 0.7 mol) and CH$_2$Cl$_2$ (600.4 g). The mixture was cooled to 0-5° C. AlCl$_3$ (21.0 g, 0.158 mol) was added to the flask and rinsed in w/CH$_2$Cl$_2$ (48.4 g). Temperature reached 22° C. The mixture was cooled to 0-5° C. 10% solution of POCl$_3$ (214.7 g, 1.4 mol) in CH$_2$Cl$_2$ (92.9 g, 70 ml) was added to the flask at 0-5° C. The remaining POCl$_3$ solution and a solution of 2,2,6,6-tetramethylpiperidine (197.8 g, 1.4 mol) in CH$_2$Cl$_2$ (92.8 g, 70 ml) were simultaneously added to the flask at 0-5° C., over a 3 hour period. The mixture was stirred at 0-5° C. for 2 hours then allowed to slowly warm to room temperature. The mixture was stirred overnight then allowed to stand over the weekend. Water (210.1 g) was slowly added to the flask holding the temperature at or below 43° C. The mixture was stirred for 30 minutes. CH$_2$Cl$_2$ was distilled out of the reaction mixture until the pot temperature reached 60° C. The mixture was cooled to 55° C. 20% NaOH (883 g) was added to the reaction mixture to a pH of between 4 and 5. The product was recovered by steam distillation. An additional 50% NaOH (197 g) was added to the mixture and TMP was recovered by steam distillation. Recovered TMP=193.4 g Analysis showed a purity of 96.5% for the TMP, corresponding to a 90% recovery Conversion of 3-PNO=100%; crude product=104.3 g; yield of 2C5MP=94.5%; ratio 2C5MP/2C3MP=28.8/1

Example 17

A 2-L flask was charged with 3-PNO (76.4 g, 0.7 mol) and CH$_2$Cl$_2$ (694.6 g, 524 ml). The mixture was cooled to 0-5° C. AlCl$_3$ (21.0 g, 0.158 mol) was added in portions to the flask holding temperature <15° C. The mixture was cooled to 0-5° C. 10% solution of POCl$_3$ (214.7 g, 1.4 mol) in CH$_2$Cl$_2$ (92.8 g, 70 ml) was added to the flask at 0-5° C. The remaining POCl$_3$ solution and a solution of 2,2,6,6-tetramethylpiperidine (198.1 g, 1.402 mol) in CH$_2$Cl$_2$ (92.8 g, 70 ml) were simultaneously added to the flask over a 3 hour period at 0-5° C. The mixture was stirred at 0-5° C. for 2 hours then allowed to slowly warm to room temperature. The mixture was stirred overnight then allowed to stand over the weekend. Water (210.1 g) was slowly added to the flask holding the temperature below 40° C. CH$_2$Cl$_2$ was removed by distillation to a pot temperature of 65° C. The mixture was cooled to 45° C. 20% NaOH (700.1 g) and 50% NaOH (73.6 g) were added to the reaction mixture to a pH of 4.8. The product was recovered by steam distillation. Added 50% NaOH (208.1 g) to the reaction mixture raising the pH to >10 and steam distilled the TMP. Recovered TMP=193.9 g.

Conversion of 3-PNO=100%; crude product=93.4 g; yield of 2C5MP=87.9%; ratio 2C5MP/2C3MP=29.6/1

Example 18

A 2-L flask was charged with AlCl$_3$ (21.0 g, 0.158 mol) and CH$_2$Cl$_2$ (649.9 g, 49 ml). The mixture was cooled to 0-5° C. 3-PNO (76.4 g, 0.7 mol) in CH$_2$Cl$_2$ (92 g, 70 ml) was added to the flask at 0-5° C. Solutions of POCl$_3$ (215.0 g, 1.402 mol) in CH$_2$Cl$_2$ (92.9 g, 70 ml) and 2,2,6,6-tetramethylpiperidine (fresh batch, 197.8 g, 1.4 mol) in CH$_2$Cl$_2$ (92.9 g, 70 ml) were simultaneously added to the flask at 0-5° C. over a 3 hour period. Held flask at 0-5° C. for 2 hours then allowed to slowly warm to room temperature and stirred overnight. Water (210.2 g) was carefully added to the flask maintaining the temperature below 40° C. CH$_2$Cl$_2$ was removed by distillation until the pot temperature reached 60° C. The mixture was cooled to 43° C. 20% NaOH (718.7 g) and 50% NaOH (71.1 g) were added to the reaction mixture to a pH of 4.9. The product was recovered by steam distillation using a Dean-Stark trap. After the product steam distillation was complete, additional 50% NaOH (200.9 g) was added to the flask to increase the pH to about 10. TMP was recovered via steam distillation using a Dean-Stark trap. Recovered wet TMP=191.3 g.

Conversion of 3-PNO=100%; crude product=98.2 g; yield of 2C5MP=91.1%; ratio 2C5MP/2C3MP=31.6/1

Example 19

A 2-L flask was charged with AlCl$_3$ (21.0 g, 0.158 mol) and CH$_2$Cl$_2$ (649 g, 490 ml). The mixture was cooled to 0-5° C. A solution of 3-PNO (76.4 g, 0.7 mol) in CH$_2$Cl$_2$ (92.9 g, 70 ml) was added to the flask at 0-5° C. Solutions of POCl$_3$ (214.7 g, 1.4 mol) in CH$_2$Cl$_2$ (92.8 g, 70 ml) and 2,2,6,6-tetramethylpiperidine (recovered from earlier reaction, 198 g, 1.4 mol) were added simultaneously to the flask at 0-5° C. over a 3 hour period. TMP was dissolved in CH$_2$Cl$_2$ (92.8 g, 70 ml) for the addition. The reaction mixture was stirred (0-5° C.) for 2 hours after the addition and then allowed to slowly warm to room temperature. The mixture was stirred overnight. Water (210.0 g) was carefully added to the flask holding the temperature below 40° C. CH$_2$Cl$_2$ was removed by distillation until the pot temperature reached 65° C. The mixture was cooled below 40° C. 20% NaOH (720.3 g) and 50% NaOH (61.6 g) were added to the reaction mixture to a pH of 4.6. The product was recovered by steam distillation. After the product had been recovered, additional 50% NaOH (208.3 g) was added to the flask to raise the pH to about 10 The TMP was recovered by steam distillation. Recovered wet TMP=195.2 g Conversion of 3-PNO=100%; crude product=94.6 g; yield of 2C5MP=90.3%; ratio 2C5MP/2C3MP=29.8/1

Example 20

A 2-L flask was charged with AlCl$_3$ (30.4 g, 0.228 mol) and CH$_2$Cl$_2$ (384.8 g, 290 ml). The flask was cooled to 0-5°

C. A solution of 3-PNO (109.2 g, 1.0 mol) in $CH_2Cl_2$ (92.8 g, 70 ml) was added to the flask at 0-5° C. Solution of $POCl_3$ (306.8 g, 2.001 mol) in $CH_2Cl_2$ (92.8 g, 70 ml) and recovered 2,2,6,6 tetramethylpiperidine (lot B377/03; 282.6 g, 2.0 mol) in $CH_2Cl_2$ (92.8 g, 70 ml) were added simultaneously to the flask at 0-5° C. over a 3 hour period. The reaction mixture was stirred at 0-5° C. for 2 hours then allowed to slowly warm to room temperature and stirred overnight. Water (300.4 g) was carefully added to the flask holding the temperature at or below 40° C. $CH_2Cl_2$ was removed by distillation to a pot temperature of 75° C. The mixture was cooled to 60° C. 20% NaOH (354.0 g) and 50% NaOH (359.1 g) were added to the reaction mixture to a pH of 4.1. The product was recovered by steam distillation. After the product had been recovered, additional 50% NaOH (300.7 g) was added to the flask to raise the pH to about 10. The TMP was then recovered by steam distillation. Recovered wet TMP=280.0 g Conversion of 3-PNO=100%; crude product=121.2 g; yield of 2C5MP=82.7%; ratio 2C5MP/2C3MP=26.1/1

Example 21

A 2-L flask was charged with $AlCl_3$ (21.3 g, 0.160 mol) and $CH_2Cl_2$ (650.6 g, 490 ml). The flask was cooled to 0-5° C. A solution of 3-PNO (76.4 g, 0.7 mol) in $CH_2Cl_2$ (92.8 g, 70 ml) was added to the flask at 0-5° C. Solution of $POCl_3$ (215.1 g, 1.483 mol) in $CH_2Cl_2$ (92.8 g, 70 ml) and recovered 2,2,6,6 tetramethylpiperidine (197.8 g, 1.4 mol) in $CH_2Cl_2$ (92.9 g, 70 ml) were prepared. 10% of the TMP solution was added to the flask at 0-5° C. The remaining TMP solution and the $POCl_3$ solution were then added simultaneously to the flask at 0-5° C. over a 3 hour period. The reaction mixture was stirred for 2 hours at 0-5° C. then allowed to slowly warm to room temperature and stirred overnight. Water (210.0 g) was carefully added to the flask while maintaining the temperature below 40° C. $CH_2Cl_2$ removed by distillation to a pot temperature of 70° C. The mixture was cooled to 60° C. 20% NaOH (720.7 g) and 50% NaOH (67.0 g) were added to the reaction mixture to a pH of 4.6. The product was recovered by steam distillation. After the product had been recovered, additional 50% NaOH (222.1 g) was added to the reaction mixture raising the pH to 9.7. The TMP was recovered by steam distillation. Recovered wet TMP=99.1 g.

Conversion of 3-PNO=100%; crude product=78.4 g; yield of 2C5MP=77.5%; ratio 2C5MP/2C3MP=31.3/1

Example 22

A 2-L flask was charged with $AlCl_3$ (15.1 g, 0.113 mol) and $CH_2Cl_2$ (651.2 g, 490 ml). The flask was cooled to 0-5° C. A solution of 3-PNO (76.4 g, 0.7 mol) in $CH_2Cl_2$ (92.8 g, 70 ml) was added to the flask at 0-5° C. Solutions of $POCl_3$ (214.8 g, 1.401 mol) in $CH_2Cl_2$ (92.8 g, 70 ml) and recovered 2,2,6,6 tetramethylpiperidine (lot B377/06, 197.8 g, 1.4 mol) in $CH_2Cl_2$ (92.8 g, 70 ml) were added simultaneously to the flask at 0-5° C. over a 3 hour period. The mixture was stirred at 0-5° C. for 2 hours then allowed to slowly warm to room temperature and stirred over the weekend. Water (210.3 g) was carefully added to the flask holding the temperature at or below 40° C. $CH_2Cl_2$ was removed by distillation until the pot temperature reached 75° C. The mixture was cooled to 50° C. 20% NaOH (723.7 g) and 50% NaOH (59.4 g) were added to the reaction mixture to a pH of 4.9. The product was recovered by steam distillation. After product steam distillation was complete, 50% NaOH (209.6 g) was added to the flask to raise the pH to about 10. The TMP was recovered by steam distillation collecting the top, organic phase. Recovered wet TMP=193.8 g Conversion of 3-PNO=100%; crude product=81.4 g; yield of 2C5MP=77.2%; ratio 2C5MP/2C3MP=19.9/1

Example 23

A 2-L flask was charged with $AlCl_3$ (21.0 g, 0.157 mol) and $CH_2Cl_2$ (186.0 g, 140 ml). The flask was cooled to 0-5° C. A solution of 3-PNO (76.4 g, 0.7 mol) in $CH_2Cl_2$ (92.8 g, 70 ml) was added to the flask at 0-5° C. Solutions of $POCl_3$ (214.8 g, 1.401 mol) in $CH_2Cl_2$ (92.8 g, 70 ml) and recovered 2,2,6,6-tetramethylpiperidine (197.8 g, 1.4 mol) in $CH_2Cl_2$ (92.8 g, 70 ml lot B377106) were simultaneously added to the flask at 0-5° C. over a 3 hour period. The flask was stirred for 2 hours at 0-5° C. then allowed to slowly warm to room temperature and stirred overnight. Water (210.0 g) was carefully added to the flask holding the temperature to at or below 40° C. $CH_2Cl_2$ was removed by distillation to a pot temperature of 75° C. The mixture was cooled to 40° C. 20% NaOH (721.0 g) and 50% NaOH (56.3 g) were added to the reaction mixture to a pH of 4.2. The product was recovered by steam distillation. After the product had been recovered, 50% NaOH (211.3 g) was added to the flask to raise the pH to about. The TMP was then recovered by steam distillation. Recovered wet TMP=195.6 g Conversion of 3-PNO=100%; crude product=71.8 g; yield of 2C5MP=72.3%; ratio 2C5MP/2C3MP=26.4/1

Example 24

A 2-liter round-bottom flask equipped with stirring, external cooling, and a condenser was loaded with methylene chloride (742 g) and 3-methylpyridine N-oxide (382 g, 0.35 mol). Aluminum trichloride (11.7 g, 0.88 mol) was then added in small portions to the flask over 15 minutes. The contents were then cooled to 0 to +5° C. Phosphorus oxychloride (107.4 g, 0.70 mol) was mixed with methylene chloride (93 g) and transferred to a syringe pump and connected to the 2-liter flask. 2,2,6,6-Tetramethylpiperidine (98.9 g, 0.7 mol) was mixed with methylene chloride (93 g) and transferred to a second syringe pump and connected to the 2-liter flask. The syringe pump containing the phosphorus oxychloride solution was started and 10% of the solution was added to the 2-liter flask over 20 minutes. The syringe pump containing the tetramethylpiperidine solution was then started and co-fed to the 2-liter flask. Addition of both solutions was completed in 3 hours. After completion, the reaction contents were stirred for 2 hours. The temperature of the reaction flask was kept at 0 to +5° C. throughout this step. Water (105 g) was slowly added to the reaction flask. The temperature was allowed to rise to 35° C. The contents were stirred for 30 minutes then the methylene chloride was removed by distillation. Distillation was stopped when the pot temperature reached 60° C. The mixture was cooled below 35° C. and a 20% sodium hydroxide solution (480 g) was slowly added to the flask. The pH of the reaction mixture measured 5.2 at this point. The product and unreacted pyridines were then removed by steam distillation. The weight of the recovered pyridines was 53.3 g. Analysis showed the recovered pyridines to contain 0% 3-methylpyridine N-oxide, 93.7% 2-chloro-5-methylpyridine, 4.3% 2-chloro-3-methylpyridine, 0.1% 4-chloro-3-methylpyridine and 2.0% 3-methylpyridine, which equates 100% conversion of the 3-methylpyridine N-oxide, and 94% yield to 2-chloro-5-methylpyridine.

Example 25

To a round-bottom flask was added 680 mL dichloromethane, 161 grams phosphorus oxychloride, and 148 grams 2,2,6,6-tetramethylpiperidine. A solution of 76 grams 3-methylpyridine N-oxide in 21 mL dichloromethane was added to the reaction flask over a three hour period at 0-5° C. The reaction mixture was allowed to stir for two hours at 0-5° C. then the contents were heated and dichloromethane was distilled from the mixture until the pot temperature reached 140° C. The reaction mixture was held at 140° C. for 3.5 hours and then cooled to 90° C. Dichloromethane (100 mL) was added back to the flask and mixture was cooled to room temperature. Water (310 grams) was slowly added to the reaction flask while maintaining the reaction temperature below 45° C. After the water addition, dichloromethane was removed by distillation until the pot temperature reached 70° C. The reaction mixture was cooled to 35° C. and 173 grams 50% sodium hydroxide was added to the flask raising the pH to between 4 and 5. Crude, wet chloromethylpyridines (94.6 grams) were recovered from the reaction mixture by steam distillation. Analysis showed the chemical yield of 2-chloro-5-methylpyridine was 79%, and the 2-chloro-5-methylpyridine/2-chloro-3-methylpyridine isomer ratio was 24/1.

To the reaction mixture remaining in the flask, an additional 220 grams 50% sodium hydroxide was added to bring the pH >9.0. Steam distillation was continued to recover 139 grams crude, wet 2,2,6,6-tetramethylpiperidine. Analysis showed the assay=96.5% corresponding to a 90% recovery.

Comparative Example 1

A 2-L flask was charged with 3-PNO (38.2 g, 0.35 mol), $CH_2Cl_2$ (742.1 g, 560 ml), and cooled to 0-5° C. 10% of a solution of $POCl_3$ (107.8 g, 0.703 mol) in $CH_2Cl_2$ (92.8 g, 70 ml) was added to the flask. The remaining $POCl_3$ solution and a solution of diisobutylamine (91.4 g, 0.707 mol) in $CH_2Cl_2$ (92.8 g, 70 ml) were added co-currently to the flask over a 3 hour period at 0-5° C. The mixture was stirred for 2 hours at 0-5° C., and allowed to stand over the weekend. Water (105.2 g) was slowly added to the flask holding the temperature at or below 22° C. The mixture was stirred for 30 minutes then $CH_2Cl_2$ was removed by distillation to a pot temperature of 70° C. The mixture was cooled to 20-25° C. 20% NaOH (400.0 g) was added to the reaction mixture at 20-25° C. to a pH of 7.3. The product was recovered by steam distillation.

Conversion of 3-PNO=99.7%; crude product=50.1 g; yield of 2C5MP=16%; ratio 2C5MP/2C3MP=1.0/1

Comparative Example 2

A 2-L flask was charged with 3-PNO (38.2 g, 0.35 mol), $CH_2Cl_2$ (742.2 g, 560 ml). The mixture was cooled to 0-5° C. 10% of a solution of $POCl_3$ (107.7 g, 0.702 mol) in $CH_2Cl_2$ (92.9 g, 70 ml) was added to the flask at 0-5° C. The remaining $POCl_3$ solution and a solution of tributylamine (129.9 g, 0.7 mol) in $CH_2Cl_2$ (92.9 g, 70 ml) were adding co-currently over a 3 hour period at 0-5° C. The mixture was stirred for 2 hours at 0-5° C. Stood overnight at room temperature. Water (105.0 g) was carefully added to the flask holding temperature below 40° C. $CH_2Cl_2$ was removed by distillation to a pot temperature of 70° C. 20% NaOH (452.0 g) was added to the reaction mixture raising the pH to 5.4 holding temperature at 30-35° C. The product was recovered by steam distillation.

Conversion of 3-PNO=100%; crude product=105.1 g; yield of 2C5MP=32%; ratio 2C5MP/2C3MP=4.2/1

Comparative Example 3

A 2-L flask was charged with 3-PNO (38.2 g, 0.35 mol) and $CH_2Cl_2$ (742.3 g, 560 ml). The mixture was cooled to 0-5° C. 10% of a solution of $POCl_3$ (107.6 g, 0.702 mol) in $CH_2Cl_2$ (92.9 g, 70 ml) was added to the flask at 0-5° C. The remaining $POCl_3$ solution and a solution of diisopropylamine (DIA) (70.8 g, 0.7 mol) in $CH_2Cl_2$ (92.8 g, 70 ml) were added co-currently over a 3 hour period to the flask at 0-5° C. The mixture was stirred at 0-5° C. for 2 hours then allowed to slowly warm to room temperature while stirring overnight. Water (105.1 g) was carefully added to the flask holding the temperature at or below 30° C. The mixture was stirred 30 minutes. $CH_2Cl_2$ was removed by distillation to a pot temperature of 60° C. The mixture was cooled to 35° C. 20% NaOH (413.8 g) was added to the reaction mixture to a pH of 5.3 holding the temperature below 40° C. The product was recovered by steam distillation.

Conversion of 3-PNO=100%; crude product=47.4 g; yield of 2C5MP=69.4%; ratio 2C5MP/2C3MP=5.3/1

Comparative Example 4

A 2-L flask was charged with 3-PNO (0.35 mol) and $CH_2Cl_2$ (38.2 g, 560 ml). The mixture was cooled to 0-5° C. 10% of a solution of $POCl_3$ (107.9 g, 0.704 mol) in $CH_2Cl_2$ (98.2 g, 70 ml) was added to the flask at 0-5° C. The remaining $POCl_3$ solution and a solution of triethylamine (70.9 g, 0.7 mol) in $CH_2Cl_2$ (92.9 g, 70 ml) were added to the flask co-currently at 0-5° C. over a 3 hour period. The mixture was stirred for 2 hours at 0-5° C., allowed to slowly warm to room temperature and stirred overnight. Water (105.0 g) was carefully added to the flask holding the temperature below 40° C. The mixture was stirred 30 minutes. $CH_2Cl_2$ was removed by distillation to a pot temperature was 60° C. The mixture was cooled to 25° C. 20% NaOH (428.8 g) was added to the reaction mixture to a pH of 5.0 holding the temperature at or below 35° C. The product was recovered by steam distillation.

Conversion of 3-PNO=100%; crude product=53.6 g; yield of 2C5MP=53.4%; ratio 2C5MP/2C3MP=4.5/1

Comparative Example 5

A 2-L flask was charged with 3-PNO (38.2 g, 0.35 mol) and $CH_2Cl_2$ (742.3 g, 560 ml). The mixture was cooled to 0-5° C. 10% of a solution of $POCl_3$ (107.3 g, 0.7 mol) in $CH_2Cl_2$ (92.9 g, 70 ml) was added to the flask at 0-5° C. The remaining $POCl_3$ solution and a solution of diisopropylamine (70.8 g, 0.7 mol) in $CH_2Cl_2$ (93.0 g, 70 ml) were added to the flask co-currently at 0-5° C. over a 3 hour period. The mixture was stirred for 2.5 hours at 0-5° C. Water (305.8 g) was carefully added to the flask holding temperature below 35° C. Transferred the mixture to a separatory funnel and separated layers. The bottom, organics layer was concentrated on the roto-vap to give crude product.

Conversion of 3-PNO=98%; crude product=76.4 g; yield of 2C5MP=37.2%; ratio 2C5MP/2C3MP=6.4/1

TABLE 1

| Example | Amine Utilized | 2-chloro-5-methylpyridine yield | 2-chloro-5-methyl/2-chloro-3-methyl isomer ratio |
|---|---|---|---|
| 1 | diisooctylamine | 14% | 1.1/1 |
| 3 | dicyclohexylamine | 63% | 5.0/1 |
| 4 | 2,6-lupetidine | 65% | 2.9/1 |
| 5 | N,N-diisopropylethylamine | 46% | 9.3/1 |
| 25 | 2,2,6,6-tetramethylpyridine (TMP) | 79% | 24/1 |
| CE-1 | diisobutylamine | 16% | 1.0/1 |
| CE-2 | tributylamine | 32% | 4.2/1 |
| CE-3 | diisopropylamine (DIA) | 69% | 5.3/1 |
| CE-4 | triethylamine | 53% | 4.5/1 |

TABLE 2

| Example | Amine | Eq. $AlCl_3$ | 3PNO Conversion, % | Selectivity 2C5MP, % | Selectivity 2C3MP, % |
|---|---|---|---|---|---|
| CE-3 | DIA | 0.00 | 100% | 81% | 15% |
| 11 | DIA | 0.25 | 100% | 87% | 11% |
| 2 | TMP | 0.00 | 100% | 92% | 5% |
| 12 | TMP | 0.25 | 100% | 94% | 4% |

| Example | Amine | Eq. $AlCl_3$ | Selectivity 4C3MP, % | Selectivity 3-Picoline, % | Yield 2C5MP |
|---|---|---|---|---|---|
| CE-3 | DIA | 0.00 | 1% | 3% | 69% |
| 11 | DIA | 0.25 | 0% | 2% | 84% |
| 2 | TMP | 0.00 | 1% | 2% | 74% |
| 12 | TMP | 0.25 | 0% | 2% | 94% |

What is claimed is:

1. A process for preparing 2-chloro-5-methylpyridine, the process comprising the step of:
    a) contacting 3-methylpyridine N-oxide in a diluent, at a first temperature of about −20° C. to about 20° C., with phosphoryl oxychloride ($POCl_3$), and 2,2,6,6-tetramethylpiperidine.

2. The process of claim 1 further comprising the step of
    b) contacting the 3-methylpyridine N-oxide in the diluent with aluminum chloride ($AlCl_3$) prior to contacting with $POCl_3$, and the 2,2,6,6-tetramethylpiperidine.

3. The process of claim 2 wherein the amount of $AlCl_3$ per mole of 3-methylpyridine N-oxide is about 0.1 mole to about 0.3 mole.

4. The process of claim 2 wherein the amount of $AlCl_3$ per mole of 3-methylpyridine N-oxide is about 0.2 mole to about 0.25 mole.

5. The process of claim 1 wherein the diluent is selected from pentane, hexane, heptane, octane, cyclohexane, methylcyclohexane, petroleum ether, naphtha, ligroin, benzene, toluene, xylenes, methylene chloride, chloroform, tetrachloromethane, 1,2-dichloroethane, chlorobenzene, dichlorobenzene, diethyl ether, dipropyl ether, diisopropyl ether, dibutyl ether, methyl tert-butyl ether, glycol dimethyl ether, diglycol dimethyl ether, tetrahydrofuran, dioxane, methyl acetate, ethyl acetate, propyl acetate, butyl acetate amyl acetate, acetonitrile, and propionitrile.

6. The process of claim 1 wherein the diluent is methylene chloride.

7. The process of claim 1 wherein the amount of $POCl_3$ per mole of 3-methylpyridine N-oxide is about 1 to about 5 moles.

8. The process of claim 1 wherein the amount of $POCl_3$ per mole of 3-methylpyridine N-oxide is about 1.5 to about 2.5 moles.

9. The process of claim 1 wherein the amount of $POCl_3$ per mole of 3-methylpyridine N-oxide is about 2 moles.

10. The process of claim 1 wherein the amount of the 2,2,6,6-tetramethylpiperidine per mole of 3-methylpyridine N-oxide is about 1 to about 5 moles.

11. The process of claim 1 wherein the amount of the 2,2,6,6-tetramethylpiperidine per mole of 3-methylpyridine N-oxide is about 1.5 to about 2.5 moles.

12. The process of claim 1 wherein the amount of the 2,2,6,6-tetramethylpiperidine per mole of 3-methylpyridine N-oxide is about 2 moles.

13. The process of claim 1 further comprising the step of
    b) heating the resulting mixture from step a) to a second temperature while removing a portion of the diluent by distillation.

14. The process of claim 2 further comprising the step of
    c) holding the mixture resulting from step b) at the second temperature for a period of time, wherein the second temperature is from about 50° C. to about 150° C.

* * * * *